United States Patent [19]

Nakanishi

[11] 3,957,811

[45] May 18, 1976

[54] PROCESS FOR 3-(1-[ARYLMETHYL]TETRAZOL-5-YL)PENAMS

[75] Inventor: Susumu Nakanishi, East Lyme, Conn.

[73] Assignee: Pfizer Inc., New York, N.Y.

[22] Filed: Oct. 9, 1974

[21] Appl. No.: 513,214

[52] U.S. Cl. .......................... 260/306.7 R; 424/270; 424/271

[51] Int. Cl.$^2$ .......................... C07D 498/04

[58] Field of Search .................. 260/308 D, 306.7 R

[56] References Cited

UNITED STATES PATENTS

| | | | |
|---|---|---|---|
| 3,138,609 | 6/1964 | Carpenter | 260/308 D |
| 3,839,339 | 10/1974 | Ellis et al. | 260/308 D |

OTHER PUBLICATIONS

Elderfield, (ed.), *Heterocyclic Compounds*, Vol. 8, 1967, N.Y.C., Wiley, pp. 21 and 32.

*Primary Examiner*—Raymond V. Rush
*Attorney, Agent, or Firm*—Connolly and Hutz

[57] ABSTRACT

A process for the synthesis of 6-(triphenylmethylamino)-2,2-dimethyl-3-(1-[arylmethyl]tetrazol-5-yl)penams, intermediates useful in the preparation of antibiotic penams, which comprises contacting in a reaction-inert solvent a 6-(triphenylmethylamino)-2,2-dimethyl-3-(alkyl- or arylsulfonyloxy[N-(arylmethyl)imino]methyl)penam with one to three equivalents of hydrazoic acid or with an ammonium, sodium or lithium azide at a reaction temperature of 20°–60° C., in the presence of more than one equivalent of pyridine.

7 Claims, No Drawings

PROCESS FOR 3-(1-[ARYLMETHYL]TETRAZOL-5-YL)PENAMS

BACKGROUND OF THE INVENTION

1. Field of the Invention

Methods used to synthesize tetrazoles vary widely depending on the availability of the starting reagents and the structure of the final product desired. It has now been discovered that 1,5-disubstituted tetrazoles, which are valuable intermediates leading to useful antibacterial agents, can be prepared from the reaction of an imino sulfonate, synthesized through the reaction of an appropriate amide and a sulfonyl chloride, with a source of azide ion.

2. Description of the Art

Tetrazoles, the physical and chemical properties and synthesis thereof, have recently been reviewed by F. R. Benson in "Heterocyclic Compounds," Vol. 8, R. C. Elderfield, Ed., John Wiley and Sons, Inc., New York, N.Y., 1967, Chapter 1.

Sinnema, et al., Rec. trav. chim., 76, 949 (1957) reports the preparation of 5-phenyltetrazole by the azide displacement of the ethoxy moiety of ethyl benzimidate, while the synthesis of 1,5-disubstituted tetrazoles from the corresponding imino chloride and sodium azide is reported by Schroeter, Ber., 42, 3356 (1909), Smith, et al., J. Am. Chem. Soc., 80, 4647 (1958) and Vaughan, et al., J. Org. Chem., 23, 1909 (1958). Synthesis of mono- and disubstituted tetrazoles by the reaction of an imino chloride with hydrazoic acid in an aromatic solvent is taught by Harvill, et al., J. Org. Chem., 15, 662 (1950) and Fallon, et al., J. Org. Chem., 22, 933 (1957).

SUMMARY OF THE INVENTION

It has now been unexpectedly found that compounds of the formula

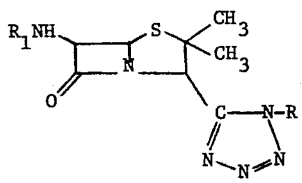

wherein R is substituted benzyl of the formula

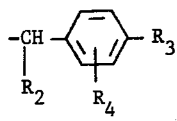

wherein $R_2$ is hydrogen, alkyl having from one to three carbon atoms or phenyl and $R_3$ is hydroxy, methoxy, alkanoyloxy having two to four carbon atoms, or benzyloxy and $R_4$ is hydrogen, hydroxy, fluoro, chloro, bromo, iodo, methyl, methoxy, alkanoyloxy having from two to four carbon atoms, phenyl or benzyloxy, or

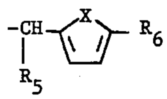

wherein $R_5$ and $R_6$ are each hydrogen or methyl and X is oxygen or sulfur; and $R_1$ is

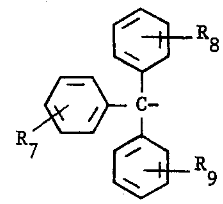

where $R_7$, $R_8$ and $R_9$ are each hydrogen, chloro, bromo, fluoro, methyl, methoxy or phenyl can be prepared by a process which comprises contacting in a reaction-inert solvent an imino sulfonate of the formula

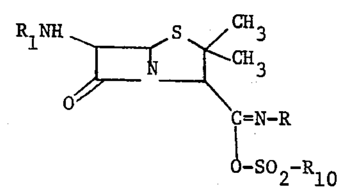

wherein $R_{10}$ is alkyl having 1 to 4 carbon atoms, phenyl or substituted phenyl wherein said substituent is methyl or nitro, with one to three equivalents of an azide of the formula $MN_3$ wherein M is $NH_4$, Li, H or Na, at a reaction temperature of 20°–60° C. in the presence of more than one equivalent of pyridine.

A preferred feature of the present process is the preparation of tetrazoles wherein R is p-methoxybenzyl, $R_1$ is triphenylmethyl, $R_{10}$ is methylphenyl or alkyl having 1 to 4 carbon atoms and M is Na, at a reaction temperature of about 25° C.

DETAILED DESCRIPTION OF THE INVENTION

The aforementioned reaction is depicted in the following scheme

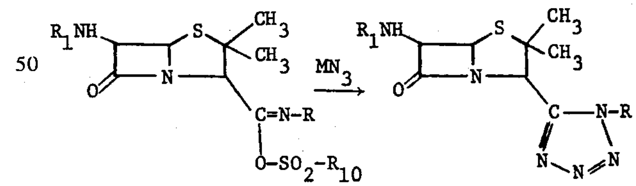

wherein R, $R_1$, $R_{10}$ and M are as previously defined.

Experimentally, conversion of the imino sulfonate to the corresponding tetrazole is carried out in a reaction-inert solvent, said solvent being one which appreciably solubilizes the reactants without reacting to any appreciable extent with either the reactant or the products under the reaction conditions. The preferred solvents include dimethylformamide, dimethylacetamide, acetonitrile and chloroform; the especially preferred solvent is chloroform.

The molar ratio of reactants can vary considerably. For each mole of imino sulfonate there is required at least one mole of the azide $MN_3$, while larger amounts can be employed without markedly affecting the course of the reaction or the yield of desired product. The toxicity of hydrazoic acid, $HN_3$, and the explosive nature of certain metal azides, however, favor the commercial use of a minimal excessive amount of this reactant. Accordingly, from 1 to 3 moles of $MN_3$ per mole of imino sulfonate is preferred.

Although pyridine's precise role in the present process is not clearly understood, its presence, or that of some other tertiary amine, is essential for formation of the useful product. When one equivalent of pyridine per mole of imino sulfonate is employed, the reaction proceeds, but at such a slow rate as to render it impractical. Accordingly, amounts of pyridine, or its equivalent, up to and including six equivalents of pyridine can be used without markedly affecting the outcome of the reaction or the quality of the final product, but such quantities offer no practical advantages.

Reaction time is not critical and is inherently dependent on concentration, reaction temperature and reactivity of the starting reagents. In general, when ambient reaction temperatures are employed, the reaction time is 24-48 hours. The time required for completion of the present process is reduced as the reaction temperature is increased.

The preferred reaction temperatures are those which allow the reaction to proceed at a practical rate without resulting in thermal degradation of the starting reagents or the products of said process. Accordingly, temperatures of 25°–60° C. are operable, with a preferred range of about 25°–30° C.

The order of addition of the reactants is not critical. Because of the labile nature of imino sulfonates, it is preferred that these intermediates not be isolated. Consequently, it is preferred that the appropriate imino sulfonate be prepared in situ from the corresponding amide and sulfonyl halide. It is further preferred that the pyridine and azide be added to a solution of the imino sulfonate in an appropriate reaction-inert solvent. As one skilled in the art can readily appreciate, the purity of the final product, in this case the tetrazole of the present process, is determined to a large degree by the completeness of the reaction and the purity of the starting reagents. To achieve maximum purity of the aforementioned tetrazole, it is desirable to employ as purified an amide as practically possible for the in situ synthesis of the imino sulfonate starting material.

At the completion of the present process, the reaction mixture is quenched in water and the product isolated by filtration or decantation. The product is subsequently triturated or recrystallized from an appropriate solvent and used in subsequent reactions.

As previously mentioned, the product of the present process is a useful intermediate leading to other penams having antibacterial activity and useful themselves in combating bacterial infections. A flow diagram showing the conversion of the product from the instant process to antibacterial penams is depicted as follows:

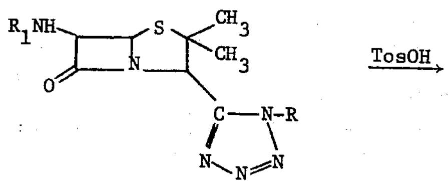

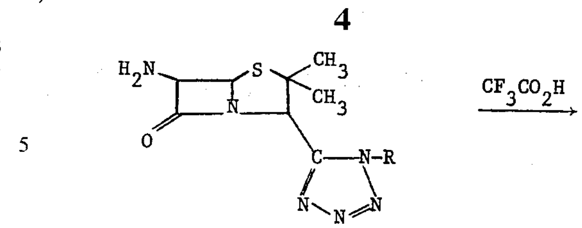

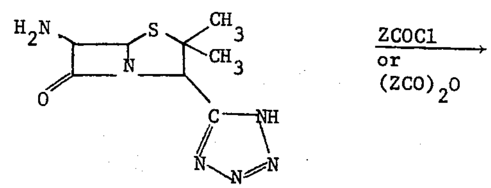

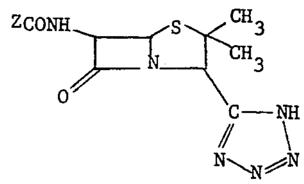

wherein R and $R_1$ are as previously defined, and ZCOCl and$(ZCO)_2O$ are acylating agents.

In the first step of this conversion, the 6-amino group is deblocked by removal of the triphenylmethyl moiety with p-toluenesulfonic acid or a hydrate thereof. It is preferred that said reaction be conducted in a reaction-inert solvent which will facilitate precipitation of the resulting tosylate acid addition salt and also solubilize the starting reagents. Such solvents as ethers, dialkyl ketones or chlorinated hydrocarbons are suitable, with the preferred solvent being acetone.

Experimentally, one mole of the p-toluenesulfonic acid is contacted with an equimolar amount of the penam derivative in the appropriate solvent for from 1 to 60 minutes at ambient temperatures. The resulting tosylate salt of the product is filtered. The crude product can be used as isolated or may be triturated in a suitable solvent. The free amino compound can be isolated from the salt in the usual manner, but since p-toluenesulfonic acid is used in the next step of the sequence, it is advantageous to utilize the acid addition salt as isolated.

The next step in the synthetic route leading to final antibacterial products, prepared from the products of the instant process, is removal of the penam tetrazole protecting group, R.

In practice, the tosylate acid addition salt in anisole is treated with an excess of trifluoroacetic acid at $40 \pm 5°$ C. for from 5-45 minutes. The trifluoroacetic acid acts as reagent and solvent in this solvolysis reaction.

Following completion of the reaction, the excess trifluoroacetic acid and anisole are removed under reduced pressure and the residual trifuoroacetic acid addition salt treated with base and acid under extracting conditions familiar to those skilled in the art, to generate the free 6-amino-2,2-dimethyl-3-(tetrazolyl)penam.

Acylation of the above-mentioned product is carried out by a procedure familiar to one skilled in the art. The acylating species, either an acid halide or anhydride, is added to 6-amino-2,2-dimethyl-3-(tetrazolyl)penam in a solution of chloroform containing at least two equivalents of a tertiary amine such as triethylamine or pyridine. The reaction time is approximately 10–60 min. at ambient temperatures. The product is isolated by quenching the reaction mixture in water, followed by removal of basic material through an acid wash and subsequent extraction of the product from the chloroform with aqueous base. Acidification of the aqueous solution liberates the product, which can be filtered or extracted with a water immiscible solvent.

The requisite imino sulfonate is generated by a series of reactions starting with commercially available 6-aminopenicillanic acid as follows:

methoxybenzyl, $R_1$ is triphenylmethyl, $R_{10}$ is p-tolyl or methyl, M is Na and the reaction temperature is about 25° C.

A second preferred feature of the instant process is the preparation of tetrazoles where R is 2-furfuryl, $R_1$ is triphenylmethyl, $R_{10}$ is p-tolyl or methyl, M is Na and the reaction temperature is about 25° C.

The antibacterial penam compounds, prepared from the products of the instant process invention, show activity against a wide variety of gram-positive and gram-negative bacteria. The in vitro activity can be demonstrated by the conventional two-fold serial dilution technique in Brain-Heart Infusion broth (Difco). The broth is inoculated with the bacterial culture, and with the test antibiotic, and then it is incubated overnight. On the next day, the test is read visually. The minimum inhibitory concentration (MIC) is the lowest concentration of antibiotic which prevents turbidity,

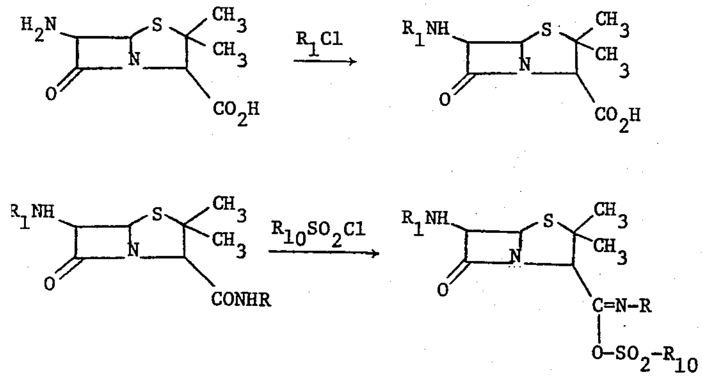

Protection of the amino moiety is carried out by the procedure of Sheehan, et al., J. Am. Chem. Soc., 81, 5838 (1959) which comprises alkylation of the 6-aminopenicillanic acid with a triphenylmethyl chloride, prepared by the method of Bachmann, Org. Syn., 23, 100 (1943).

Conversion of the 3-carboxylic acid to the appropriate amide is carried out through the mixed anhydride according to the method as taught by Barnden, et al., J. Chem. Soc., 3733 (1953).

Reaction of the amide with the appropriate sulfonyl chloride in the presence of a tertiary amine leads to the imino sulfonate. Experimentally, this reaction is best effected by reacting one mole of the amide with an equimolar amount of the sulfonyl chloride plus as much as a 100% excess in the presence of three to six moles of a tertiary amine, preferably pyridine, in a solvent, such as chloroform. When conducted at ambient temperatures, the reaction is complete within twelve to forty-eight hours. Since the imino sulfonates are relatively sensitive to hydrolysis, it is further preferred that these imino sulfonates be reacted with an azide without isolation.

An especially preferred feature of the present process if the synthesis of tetrazoles wherein R is p- i.e., which prevents growth of the microorganism. In vitro activities of several of the penam compounds of the invention are presented later in this specification.

The in vitro activity of the antibacterial compounds, synthesized from the intermediates produced by the process of the instant invention, makes them particularly suitable for topical application, for example, in the form of creams and ointments, and for the sterilization of sick-room and hospital surfaces, equipment, and the like.

These antibacterial penam compounds are also active in vivo. In determining such activity, the test antibiotic is administered to infected mice, using a multiple dosing regimen. The severity of the infection varies from about one to ten times the dose needed to kill 100% of the mice under the conditions of the test. At the end of the test, the activity of a compound is assessed by counting the number of survivors among the treated animals. Both the subcutaneous (SC) and the oral (PO) dosage routes are used. Results are given in Table I for two of the compounds of the invention. the ability of the compounds to protect mice against systemic infections caused by a lethal intraperitoneal inoculum of Staphylococcus aureus or of Escherichia coli is presented.

TABLE I

| Compound | Dosage (mg./kg.) | Dosage | Percentage Protection S. aureus | E. coli |
|---|---|---|---|---|
| 6-(D-2-amino-2-[3-thienyl]acetamido)-2,2-dimethyl-3-(5- | 50 | SC | 40 | 20 |

TABLE I-continued

| Compound | Dosage (mg./kg.) | Dosage | Percentage Protection S. aureus | E. coli |
|---|---|---|---|---|
| tetrazolyl)penam | | | | |
| " | 25 | SC | 60 | 20 |
| " | 12 | SC | 50 | |
| " | 6 | SC | 50 | |
| " | 200 | PO | | 0 |
| 6-(D-2-amino-2-[p-hydroxyphenyl]acetamido)-2,2-dimethyl-3-(5-tetrazolyl)penam | 50 | SC | 80 | 100 |
| " | 25 | SC | 70 | 80 |
| " | 12 | SC | 50 | |
| " | 6 | SC | 50 | |
| " | 200 | PO | | 100 |

The in vivo activity of these antibacterial compounds makes them suitable for the control of bacterial infections in mammals, including man, by both the oral and parenteral modes of administration. The compounds will find wide use in the control of infections caused by susceptible gram-positive and gram-negative bacteria in human subjects.

When considering therapeutic use of a compound prepared from the products formed by the present invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an aforementioned antibacterial penam cmpound can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions is suitably adjusted and buffered. For intravenous use, the total concentration of solutes should be controlled to render the preparation isotonic.

As indicated earlier, these antibacterial penam compounds are of use in human subjects and the daily dosages to be used will not differ significantly from other, clinically-used, penam antibiotics. The prescribing physician will ultimately determine the appropriate dose for a given human subject, and this can be expected to vary according to the age, weight, and response of the individual patient, as well as the nature and the severity of the patient's symptoms. These compounds will normally be used orally at dosages in the range from about 10 to about 200 mg. per kilogram of body weight per day, and parenterally as dosages from about 5 to about 100 mg. per kilogram of body weight per day. These figures are illustrative only, however, and in some cases it may be necessary to use dosages outside these limits.

The following examples are provided solely for the purpose of further illustration. Infrared (IR) spectra are measured as potassium bromide discs (KBr discs) or as Nujol mulls, and diagnostic absorption bands are reported in wave numbers ($cm^{-1}$). Nuclear magnetic resonance spectra (NMR) are measured at 60 MHz for solutions in deuterochloroform ($CDCl_3$), perdeutero dimethyl sulfoxide (DMSO-$d_6$) or deuterium oxide ($D_2O$), and peak positions are expressed in parts per million (ppm) downfield from tetramethylsilane or sodium 2,2-dimethyl-2-silapentane-5-sulfonate. The following abbreviations for peak shapes are used: s - singlet; d - doublet; t - triplet; q - quartet; m - multiplet.

EXAMPLE 1

6-(Triphenylmethylamino)-2,2-dimethyl-3-(1-[p-methoxybenzyl]tetrazol-5-yl)penam

A. 6-(Triphenylmethylamino)-2,2-dimethyl-3-(N-[p-methoxybenzyl]carbamoyl)-penam To a stirred slurry of 216 g. of 6-aminopenicillanic acid in 1,500 ml. of anhydrous chloroform is added 278 ml. of triethylamine, and the mixture allowed to stir at ambient temperature until a clear solution is obtained. The solution is cooled to about 0° C., and 306 g. of triphenylmethyl chloride is added. The stirring is continued at about 0° C. for 30 minutes, and then at ambient temperature for a further 24 hours. The mixture is cooled to about 0° C. for 30 minutes, and then at ambient temperature for a further 24 hours. The mixture is cooled to about 0° C. again, and 14 ml. of triethylamine, followed by 95 ml. of ethyl chloroformate, is added. During this process the temperature rises to about 15° C., and a precipitate forms. To facilitate stirring a further 200 ml. of chloroform is added, and stirring continued for 30 minutes. Subsequently, 50 ml. of p-methoxybenzylamine (available from the Aldrich Chemical Company, Inc.) is injected into the reaction medium, below the surface of the solvent. At 10 minute intervals, three further aliquots of p-methoxybenzylamine (35 ml., 25 ml. and 21 ml.) are injected in the reaction in similar fashion. The total volume of p-methoxybenzylamine added is 131 ml. The cooling bath is then removed, and the reaction is stirred for an additional hour. The chloroform solution is washed successively with five 2,000-ml. portions of water and one 2,000-ml. portion of saturated brine. The chloroform is finally dried using anhydrous sodium sulfate.

Examination of the reaction mixture at this point by NMR spectroscopy, reveals that the conversion into amide is approximately 85% complete. Accordingly, the chloroform solution is cooled in an ice-bath and 21 ml. of triethylamine, followed in about 5 minutes by 14.2 ml. of ethyl chloroformate, is added. After a further 15 minutes, 9.8 ml. of p-methoxybenzylamine is added, and then in another 5 minutes a further 9.8 ml. of p-methoxybenzylamine is added. The reaction is concentrated in vacuo giving 6-triphenylmethylamino)2,2-dimethyl-3-(N-[p-methoxybenzyl]carbamoyl)penam, as an amorphous solid. Further purification can be carried out by recrystallization from isopropanol.

B.

6-(Triphenylmethylamino)-2,2-dimethyl-3-(methylsulfonyloxy-[N-(p-methoxybenzylimino]methyl)penam To 11.52 g. of crystalline 6-(triphenylmethylamino)-2,2-dimethyl-3-(N-[p-methoxybenzyl]carbamoyl)penam in 40 ml. of chloroform under a nitrogen atmosphere and cooled to 0°–5° C. is added 4.8 ml. of (3 equivalents) of pyridine followed by the dropwise addition of 2.76 g. of methylsulfonyl chloride. After allowing the reaction mixture to stir at room temperature for 6 hrs., an additional 1.5 g. of methylsulfonyl chloride and 4.8 ml. of pyridine are added. After 48 hrs. at room temperature assay by NMR spectroscopy reveals that the formaton of the imino sulfate is complete.

C.

6-(Triphenylmethylamino)-2,2-dimethyl-3-(1-[p-methoxybenzyl]tetrazol-5-yl)penam

To the reaction mixture of 6-(triphenylmethylamino)-2,2-dimethyl-3-(methylsulfonyloxy-[N-(p-methoxybenzylimino]methyl)penam in chloroform prepared in Example 1-B is added 2.6 g. (2 equivalents) of sodium azide followed by 9.6 ml. (6 equivalents) of pyridine, and the resulting mixture allowed to stir at room temperature for 48 hrs. The mixture is subsequently quenched in water (150 ml.), and the solids filtered from the biphasic system and dried, 4.8 g. The crude solid is triturated with water and recrystallized from water, 3.14 g., 178°–182° C. The infrared spectrum (KBr disc) of the products shows an absorption band at 1790 $cm^{-1}$ ($\beta$-lactam carbonyl). The NMR spectrum (in $CDCl_3$) shows absorption bands at 7.25 ppm (multiplet, aromatic hydrogens), 5.50 ppm (broad singlet, benzyl hydrogens), 5.05 ppm (singlet, C-3 hydrogen), 4.40 ppm (broad singlet, C-5 and C-6 hydrogens), 3.80 ppm (singlet, methoxy hydrogens), 1.45 ppm (singlet, C-2 methyl hydrogens) and 0.70 ppm (singlet, C-2 methyl hydrogens).

EXAMPLE 2

Starting with 6-aminopenicillanic acid, the requisite triphenylmethyl chloride and the appropriate amine and sulfonyl chloride, the process procedure of Example 1A-C is repeated, employing the indicated azide and reaction temperature:

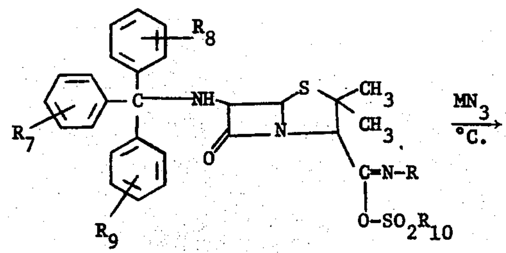

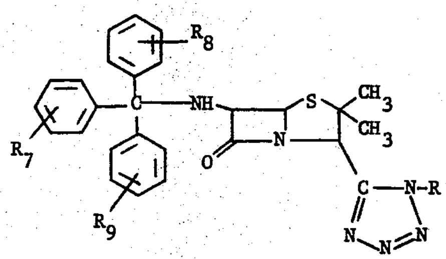

| R | $R_7$ | $R_8$ | $R_9$ | $R_{10}$ | M | Reaction Temperature, ° C. |
|---|---|---|---|---|---|---|
| $4-C_6H_5CH_2OC_6H_4CH_2$— | H— | H— | $4-CH_3$— | $CH_3$ | $NH_4$ | 25 |
| $4-C_6H_5CH_2O-3-FC_6H_3CH_2$— | H— | H— | $2-CH_3$— | $CH_3$ | Na | 25 |
| $2-Cl-4-CH_3OC_6H_3CH_2$— | H— | H— | $3-CH_3O$— | $CH_3$ | Na | 25 |
| $3-Cl-4-HOC_6H_3CH_2$— | H— | H— | $4-CH_3O$— | $CH_3$ | Na | 25 |
| $3,4-(CH_3O)_2C_6H_3CH_2$— | H— | H— | 2-F— | $CH_3$ | Na | 25 |
| $4-HOC_6H_4CH(CH_3)$— | H— | H— | 4-F— | $CH_3$ | Li | 40 |
| $2-Br-4-CH_3OC_6H_3CH_2$— | H— | H— | 3-Cl— | $C_2H_5$ | Li | 35 |
| $4-CH_3OC_6H_4CH(0)$— | H— | H— | 4-Cl— | $C_2H_5$ | Li | 35 |
| $2,4-(CH_3O)_2C_6H_3CH(CH_3)$— | H— | H— | 4-Br— | $C_2H_5$ | $NH_4$ | 50 |
| $4-CH_3OC_6H_4CH(n-C_3H_7)$— | H— | $4-CH_3$— | $4-CH_3$— | $C_2H_5$ | Li | 25 |
| $3-CH_3-4-CH_3OC_6H_3CH_2$— | H— | $4-CH_3$— | $4-CH_3$— | $C_2H_5$ | $NH_4$ | 60 |
| $4-C_2H_5CO_2C_6H_4CH_2$— | H— | $4-CH_3$— | $4-CH_3O$— | $n-C_3H_7$ | Na | 25 |
| $3-F-4-CH_3CO_2C_6H_3CH_2$— | H— | $4-CH_3O$— | $4-CH_3O$— | $n-C_3H_7$ | $NH_4$ | 25 |
| $4-HOC_6H_4CH(0)$— | H— | $3-CH_3O$— | 3-F— | $n-C_3H_7$ | Na | 20 |
| $3-I-4-CH_3OC_6H_3CH_2$— | H— | $3-CH_3O$— | 4-F— | $n-C_3H_7$ | Li | 25 |
| $4-(i-C_3H_7CO_2)C_6H_4CH_2$— | H— | $3-CH_3O$— | 4-F— | $i-C_3H_7$ | Li | 50 |
| $3,4-(C_6H_5CH_2O)_2C_6H_3CH_2$— | H— | 4-Cl— | 3-Cl— | $i-C_3H_7$ | Na | 25 |
| $4-CH_3OC_6H_4CH(CH_3)$— | H— | 4-Cl— | 4-F— | $n-C_4H_9$ | Na | 25 |
| $4-CH_3OC_6H_4CH(C_2H_5)$— | H— | 4-Cl— | 4-Br— | $n-C_4H_9$ | Li | 30 |
| $3-F-4-CH_3OC_6H_3CH_2$— | H— | 4-Br— | 4-Br— | $n-C_4H_9$ | Li | 30 |
| $3-Cl-4-CH_3OC_6H_3CH(CH_3)$— | H— | 3-Br— | $4-CH_3O$— | $n-C_4H_9$ | $NH_4$ | 40 |
| $4-HOC_6H_4CH_2$— | H— | 4-Br— | $4-CH_3$— | $n-C_4H_9$ | $NH_4$ | 60 |
| $4-CH_3CO_2C_6H_4CH_2$— | H— | H— | $C_6H_5$— | $s-C_4H_9$ | Li | 25 |
| $3-F-4-HOC_6H_3CH_2$— | H— | $C_6H_5$— | $C_6H_5$— | $s-C_4H_9$ | Na | 50 |
| $3-CH_3O-4-CH_3CO_2C_6H_4CH_2$— | $2-CH_3$— | $2-CH_3$— | $4-CH_3$— | $s-C_4H_9$ | $NH_4$ | 25 |
| $4-C_6H_5CH_2OC_6H_3CH(CH_3)$— | $4-CH_3O$— | $4-CH_3$— | $4-CH_3$— | $s-C_4H_9$ | Na | 25 |
| $3-Cl-4-C_6H_5CH_2OC_6H_3CH_2$— | $4-CH_3$— | 2-Cl— | $4-CH_3$— | $CH_3$ | $NH_4$ | 25 |
| $3,4-(C_2H_5CO_2)_2C_6H_3CH_2$— | $4-CH_3$— | 4-Br— | $4-OCH_3$— | $CH_3$ | Na | 25 |
| $4-(n-C_3H_7CO_2)C_6H_4CH_2$— | $4-CH_3$— | $4-CH_3$— | $4-CH_3$— | $CH_3$ | Na | 25 |
| $4-(i-C_3H_7CO_2)C_6H_4CH(C_2H_5)$— | $4-CH_3$— | $4-CH_3$— | $4-CH_3$— | $CH_3$ | Na | 25 |

-continued

| R | $R_7$ | $R_8$ | $R_9$ | $R_{10}$ | M | Reaction Temperature, ° C. |
|---|---|---|---|---|---|---|
| 2-furylmethyl— | 4-$CH_3$— | 4-$C_6H_5$— | 4-Cl— | $CH_3$ | Na | 25 |
| 5-methyl-2-furylmethyl— | 4-Cl— | 2-Cl— | 4-Cl— | $CH_3$ | Li | 40 |
| 2-thienylmethyl— | 3-Cl— | 4-$CH_3$— | 4-$CH_3$— | $C_2H_5$ | Li | 35 |
| 5-methyl-2-thienylmethyl— | 4-$CH_3O$— | 4-$CH_3O$— | 4-$CH_3O$— | $C_2H_5$ | Li | 35 |
| 1-(2-furyl)ethyl— | 4-F— | 4-Br— | 4-F— | $C_2H_5$ | $NH_4$ | 50 |
| 1-(5-methyl-2-furyl)ethyl— | 2-Cl— | 2-F— | 4-Br— | $C_2H_5$ | Li | 25 |

EXAMPLE 3

6-(Triphenylmethylamino)-2,2-diphenyl-3-(1-[p-methoxybenzyl]tetrazol-5-yl)penam By a procedure similar to Example 1B-C, 11.52 g. of crystalline 6-(triphenylmethylamino)-2,2-dimethyl-3-(N-[p-methoxybenzyl]carbamoyl in 40 ml. of chloroform at room temperature is treated with 4.82 ml. (3 equivalents) of pyridine. To the resulting solution is added 3.81 g. of p-toluenesulfonyl chloride and an additional 4.82 ml. of pyridine, and the stirring continued at room temperature for 8 hrs. One gram of p-toluenesulfonyl chloride is added and the reaction mixture allowed to stir for 48 hrs.

To the solution of 6-(triphenylmethylamino)-2,2-dimethyl-3-(p-tolylsulfonyloxy-[N-(p-methoxybenzylimino]methyl)penam prepared above is added 1.63 g. (1.25 equivalents) of sodium azide and the mixture allowed to stir at room temperature for 24 hours. The mixture is quenched in 3 l. of ice water and the biphasic system allowed to stir for 15 min. The resulting oily solid is filtered, trituated with water and subsequently recrystallized from chloroformisopropanol, 3.38 g., m.p. 177°–180° C. Further recrystallization raises the melting point to 186°–188° C., and provides a product which is essentially one spot in a benzene(200):ethyl acetate(10) silica gel chromatography system and indistinguishable from the final product of Example 1.

EXAMPLE 4

The process procedure of Examples 1 and 3 is repeated, starting with 6-aminopenicillanic acid, the appropriate triphenylmethyl chloride and sulfonyl chloride, and the requisite amine and employing the indicated azide and reaction temperature:

| R | $R_7$ | $R_8$ | $R_9$ | $R_{10}$ | M | Reaction Temperature, °C. |
|---|---|---|---|---|---|---|
| 4-$C_6H_5CH_2OC_6H_4CH_2$— | H— | H— | 4-$CH_3$— | p-$CH_3C_6H_4$— | $NH_4$ | 25 |
| 4-$C_6H_5CH_2O$-3-$FC_6H_3CH_2$— | H— | H— | 2-$CH_3$— | p-$CH_3C_6H_4$— | Na | 25 |
| 2-Cl-4-$CH_3OC_6H_3CH_2$— | H— | H— | 3-$CH_3O$— | p-$CH_3C_6H_4$— | Na | 25 |
| 3-Cl-4-$HOC_6H_3CH_2$— | H— | H— | 4-$CH_3O$— | p-$CH_3C_6H_4$— | Na | 25 |
| 3,4-$(CH_3O)_2C_6H_3CH_2$— | H— | H— | 2-F— | p-$CH_3C_6H_4$— | Na | 25 |
| 4-$HOC_6H_4CH(CH_3)$— | H— | H— | 4-F— | p-$CH_3C_6H_4$— | Li | 40 |
| 2-Br-4-$CH_3OC_6H_3CH_2$— | H— | H— | 3-Cl— | p-$CH_3C_6H_4$— | Li | 35 |
| 4-$CH_3OC_6H_4CH(0)$— | H— | H— | 4-Cl— | m-$CH_3C_6H_4$— | Li | 35 |
| 2,4-$(CH_3O)_2C_6H_3CH(CH_3)$— | H— | H— | 4-Br— | m-$CH_3C_6H_4$— | $NH_4$ | 50 |
| 4-$CH_3OC_6H_4CH(n\text{-}C_3H_7)$— | H— | 4-$CH_3$— | 4-$CH_3$— | m-$CH_3C_6H_4$— | Li | 25 |
| 3-$CH_3$-4-$CH_3OC_6H_3CH_2$— | H— | 4-$CH_3$— | 4-$CH_3$— | m-$CH_3C_6H_4$— | $NH_4$ | 60 |
| 4-$C_2H_5CO_2C_6H_4CH_2$— | H— | 4-$CH_3$— | 4-$CH_3O$— | m-$CH_3C_6H_4$— | Na | 25 |
| 3-F-4-$CH_3CO_2C_6H_3CH_2$ — | H— | 4-$CH_3O$— | 4-$CH_3O$— | o-$CH_3C_6H_4$— | $NH_4$ | 25 |
| 4-$HOC_6H_4CH(0)$— | H— | 3-$CH_3O$— | 3-F— | o-$CH_3C_6H_4$— | Na | 20 |
| 3-I-4-$CH_3OC_6H_3CH_2$— | H— | 3-$CH_3O$— | 4-F— | o-$CH_3C_6H_4$— | Li | 25 |
| 4-$(i\text{-}C_3H_7CO_2)C_6H_4CH_2$— | H— | 3-$CH_3O$— | 4-F— | o-$CH_3C_6H_4$— | Li | 50 |
| 3,4-$(C_6H_5CH_2O)_2C_6H_3CH_2$— | H— | 4-Cl— | 3-Cl— | o-$CH_3C_6H_4$— | Na | 25 |
| 4-$CH_{3l\ oc6}H_4CH(CH_3)$— | H— | 4-Cl— | 4-F— | p-$NO_2C_6H_4$— | Na | 25 |
| 4-$CH_3OC_6H_4CH(C_2H_5)$— | H— | 4-Cl— | 4-Br— | p-$NO_2C_6H_4$— | Li | 30 |
| 3-F-4-$CH_3OC_6H_3CH_2$ — | H— | 4-Br— | 4-Br— | p-$NO_2C_6H_4$— | Li | 30 |
| 3-Cl-4-$CH_3OC_6H_3CH(CH_3)$— | H— | 3-Br— | 4-$CH_3O$— | p-$NO_2C_6H_4$— | $NH_4$ | 40 |
| 4-$HOC_6H_4CH_2$— | H— | 4-Br— | 4-$CH_3$— | m-$NO_2C_6H_4$— | $NH_4$ | 60 |
| 4-$CH_3CO_2C_6H_4CH_2$— | H— | H— | $C_6H_5$— | m-$NO_2C_6H_4$— | Li | 25 |
| 3-F-4-$HOC_6H_3CH_2$— | H— | $C_6H_5$— | $C_6H_5$— | m-$NO_2C_6H_4$— | Na | 50 |
| 3-$CH_3O$-4-$CH_3CO_2C_6H_4CH_2$— | 2-$CH_3$— | 2-$CH_3$— | 4-$CH_3$— | m-$NO_2C_6H_4$— | $NH_2$ | 25 |
| 4-$C_6H_5CH_2OC_6H_3CH(CH_3)$— | 4-$CH_3O$— | 4-$CH_3$— | 4-$CH_3$— | o-$NO_2C_6H_4$— | Na | 25 |
| 3-Cl-4-$C_6H_5CH_2OC_6H_3CH_2$— | 4-$CH_3$— | 2-Cl— | 4-$CH_3$— | o-$NO_2C_6H_4$— | $NH_4$ | 25 |
| 3,4-$(C_2H_5CO_2)_2C_6H_3CH_2$— | 4-$CH_3$— | 4-Br— | 4-$OCH_3$— | o-$NO_2C_6H_4$— | Na | 25 |
| 4-$(n\text{-}C_3H_7CO_2)C_6H_4CH_2$— | 4-$CH_3$— | 4-$CH_3$— | 4-$CH_3$— | p-$CH_3C_6H_4$— | Na | 25 |
| 4-$(i\text{-}C_3H_7CO_2)C_6H_4CH(C_2H_5)$— | 4-$CH_3$— | 4-$CH_3$— | 4-$CH_3$— | p-$CH_3C_6H_4$— | Na | 25 |
| 2-furylmethyl— | 4-$CH_3$— | 4-$C_6H_5$— | 4-Cl— | p-$CH_3C_6H_4$— | Na | 25 |
| 5-methyl-2-furylmethyl— | 4-Cl— | 2-Cl— | 4-Cl— | p-$CH_3C_6H_4$— | Li | 40 |
| 2-thienylmethyl | 3-Cl— | 4-$CH_3$— | 4-$CH_3$— | p-$CH_3C_6H_4$— | Li | 35 |
| 5-methyl-2-thienylmethyl— | 4-$CH_3O$— | 4-$CH_3O$— | 4-$CH_3O$— | p-$CH_3C_6H_4$— | Li | 35 |
| 1-(2-furyl)ethyl— | 4-F— | 4-Br— | 4-F— | p-$CH_3C_6H_4$— | $NH_4$ | 50 |
| 1-(5-methyl-2-furyl)ethyl— | 2-Cl— | 2-F— | 4-Br— | m-$CH_3C_6H_4$— | Li | 25 |

EXAMPLE 5

6-(Triphenylmethylamino)-2,2-dimethyl-3-(1-[2-furfuryl]tetrazol-5-yl)penam

To a solution of 5.37 g. of 6-(triphenylmethylamino)-2,2-dimethyl-3-(N-[2-furfuryl]carbamoyl)penam, prepared by the procedure of Example 1-A starting with 6-aminopenicillanic acid and 2-furfuryl amine, in 50 ml. of dimethylformamide and under a nitrogen atmosphere is added 2.43 g. (1.1 equivalents) of m-nitrobenzenesulfonyl chloride followed by 4.82 ml. (6 equivalents) of pyridine. The reaction mixture is allowed to stir at room temperature overnight, and is subsequently treated with 200 ml. of benzene containing 836 mg. (2 equivalents) of hydrazoic acid. After stirring at room temperature for 36 hrs., the mixture is poured into ice water and allowed to stir for 30 min.

The oil which initially separates gradually solidifies and is triturated several times with water and, finally, filtered. Further purification is effected by recrystallization from chloroform.

EXAMPLE 6

Starting with 6-aminopenicillanic acid, the requisite triphenylmethyl chloride, the appropriate amine and sulfonyl chloride and hydrazoic acid in a benzene solution, the process procedure of Examples 1-A and 6 are repeated, employing the indicated reaction temperature.

| R | $R_7$ | $R_8$ | $R_9$ | $R_{10}$ | Reaction temperature, °C. |
|---|---|---|---|---|---|
| 4-$C_6H_5CH_2O$-3-$FC_6H_3CH_2$— | H— | H— | 2-$CH_3$— | $CH_3$ | 25 |
| 3-Cl-4-$HOC_6H_3CH_2$— | H— | H— | 4-$CH_3O$— | $CH_3$ | 25 |
| 3,4-$(CH_3O)_2C_6H_3CH_2$— | H— | H— | 2-F— | $CH_3$ | 25 |
| 4-$CH_3OC_6H_4CH(0)$— | H— | H— | 4-Cl— | $C_2H_5$ | 35 |
| 2,4-$(CH_3O)_2C_6H_3CH(CH_3)$— | H— | H— | 4-Br— | $C_2H_5$ | 50 |
| 4-$HOC_6C_4CH(0)$— | H— | 3-$CH_3O$— | 3-F— | n-$C_3H_7$ | 20 |
| 4-(i-$C_3H_7CO_2)C_6H_4CH_2$— | H— | 3-$CH_3O$— | 4-F— | i-$C_3H_7$ | 50 |
| 4-$CH_3OC_6H_4CH(C_2H_5)$— | H— | 4-Cl— | 4-Br— | n-$C_4H_9$ | 30 |
| 3-Cl-4-$CH_3OC_6H_4CH(CH_3)$— | H— | 3-Br— | 4-$CH_3O$— | n-$C_4H_9$ | 40 |
| 3-F-4-$HOC_6H_3CH_2$— | H— | $C_6H_5$— | $C_6H_5$— | s-$C_4H_9$ | 50 |
| 4-$C_6H_5CH_2OC_6H_3CH(CH_3)$— | 4-$CH_3O$— | 4-$CH_3$— | 4-$CH_3$— | s-$C_4H_9$ | 25 |
| 3,4-$(C_2H_5CO_2)_2C_6H_3CH_2$— | 4-$CH_3$— | 4-Br— | 4-$OCH_3$— | $CH_3$ | 25 |
| 4-(i-$C_3H_7CO_2)C_6H_4CH(C_2H_5)$— | 4-$CH_3$— | 4-$CH_3$— | 4-$CH_3$— | $CH_3$ | 25 |
| 2-furylmethyl— | 4-$CH_3$— | 4-$C_6H_5$— | 4-Cl— | $CH_3$ | 25 |
| 2-thienylmethyl— | 3-Cl— | 4-$CH_3$— | 4-$CH_3$— | $C_2H_5$ | 35 |
| 5-methyl-2-thienylmethyl | 4-$CH_3O$— | 4-$CH_3O$— | 4-$CH_3O$— | $C_2H_5$ | 35 |
| 1-(5-methyl-2-furyl)ethyl— | 2-Cl— | 2-F— | 4-Br— | $C_2H_5$ | 25 |
| 4-$C_6H_5CH_2OC_6H_4CH_2$— | H— | H— | 4-$CH_3$— | p-$CH_3C_6H_4$— | 25 |
| 4-$C_6H_5CH_2O$-3-$FC_6H_3CH_2$— | H— | H— | 2-$CH_3$— | p-$CH_3C_6H_4$— | 25 |
| 3,4-$(CH_3O)_2C_6H_3CH_2$— | H— | H— | 2-F— | p-$CH_3C_6H_4$— | 25 |
| 4-$CH_3OC_6H_4CH(0)$— | H— | H— | 4-Cl— | m-$CH_3C_6H_4$— | 35 |
| 3-$CH_3$-4-$CH_3OC_6H_3CH_2$— | H— | 4-$CH_3$— | 4-$CH_3$— | m-$CH_3C_6H_4$— | 60 |
| 4-$HOC_6H_4CH(0)$— | H— | 3-$CH_3O$— | 3-F— | o-$CH_3C_6H_4$— | 20 |
| 3,4-$(C_6H_5CH_2O)_2C_6H_3CH_2$— | H— | 4-Cl— | 3-Cl— | o-$CH_3C_6H_4$— | 25 |
| 4-$CH_3OC_6H_4CH(C_2H_5)$— | H— | 4-Cl— | 4-Br— | p-$NO_2C_6H_4$— | 30 |
| 4-$CH_3CO_2C_6H_4CH_2$— | H— | H— | $C_6H_5$— | m-$NO_2C_6H_4$— | 25 |
| 4-$C_6H_5CH_2OC_6H_3CH(CH_3)$— | 4-$CH_3O$— | 4-$CH_3$— | 4-$CH_3$— | o-$NO_2C_6H_4$— | 25 |
| 4-(n-$C_3H_7CO_2)C_6H_4CH_2$— | 4-$CH_3$— | 4-$CH_3$— | 4-$CH_3$— | p-$CH_3C_6H_4$— | 25 |
| 5-methyl-2-furylmethyl— | 4-Cl— | 2-Cl— | 4-Cl— | p-$CH_3C_6H_4$— | 40 |
| 2-thienylmethyl— | 3-Cl— | 4-$CH_3$— | 4-$CH_3$— | p-$CH_3C_6H_4$— | 35 |
| 1-(5-methyl-2-furyl)ethyl— | 2-Cl— | 2-F— | 4-Br— | m-$CH_3C_6H_4$— | 25 |

EXAMPLE 7

6-Amino-2,2-dimethyl-3-(5-tetrazolyl)penam

A.

6-Amino-2,2-dimethyl-3-(1-[p-methoxybenzyl]tetrazol-5-yl)penam p-toluenesulfonate To a stirred slurry of 143 g. of 6-(triphenylmethylamino)-2,2-dimethyl-3-(1-[p-methoxybenzyl]tetrazol-5yl)penam in 1,000 ml. of dry acetone at room temperature is added 45.0 g. of p-toluenesulfonic acid monohydrate, resulting in a clear solution. After about 15 min. the product starts to precipitate. Stirring is continued for a further 45 min. after the product starts to appear, and then a first crop of product is filtered off and washed with chloroform. The acetone is evaporated to dryness, and the solid residue is slurried for 45 min. in 300 ml. of chloroform. This affords a second crop of product. The two crops are combined, slurried for 1 hr. in 1,000 ml. of chloroform, filtered, and dried in vacuo, providing 123 g. of 6-amino-2,2-dimethyl-3-(1-[p-methoxybenzyl]tetrazol-5-yl)penam p-toluenesulfonate, m.p. 174°–175.5° C. The infrared spectrum (KBr disc) of the product shows an absorption band at 1795 $cm^{-1}$. The NMR spectrum (in DMSO-$d_6$) shows absorption bands at 7.20 ppm (multiplet, aromatic hydrogens), 5.80 ppm (multiplet, benzyl hydrogens, C-5 hydrogen and C-3 hydrogens), 5.20 ppm (doublet, C-6 hydrogen), 3.75 ppm (singlet, methoxy hydrogens), 2.35 ppm (singlet, sulfonate methyl hydrogens), 1.70 ppm (singlet, C-2 methyl hydrogens) and 0.85 ppm (singlet, C-2 methyl hydrogens).

B.

6-Amino-2,2-dimethyl-3-(1-[p-benzyloxybenzyl]tetrazol-5-yl)penam

A solution consisting of 558 mg. of 6-(triphenylmethylamino)-2,2-dimethyl-3-(1-[p-benzyloxybenzyl]tetrazol-5-yl)penam, 156 mg. of p-toluenesulfonic acid monohydrate and 1 ml. of acetone is stored at ambient temperature for 2.5 hrs. It is then added with stirring to 50 ml. of ether. After stirring for a further 10 min., the solid which precipitates is filtered. This affords 394 mg. of the p-toluenesulfonate of the product. A 304-mg. aliquot of this p-toluenesulfonate salt is dissolved in 10 ml. of methylene chloride, and to the solution is added 69.7 μl. of triethylamine. After 3 min., 5 ml. of water is added and the mixture is stirred vigorously. The organic phase is then separated off, diluted with ether, dried over anhydrous magnesium sulfate, and evaporated to dryness in vacuo. The residue is 189 mg. (69% yield) of 6-amino-2,2-dimethyl-3-(1-[p-benzyloxybenzyl]tetrazol-5-yl)penam. The NMR spectrum (in $CDCl_3$) of the product shows absorption bands at 7.40 ppm (singlet, phenyl hydrogens), 7.15 ppm (quartet, phenylene hydrogens), 5.55 ppm (broad singlet, C-5 and benzyl hydrogens), 5.20 ppm (singlet, C-3 hydrogens), 5.10 ppm (singlet, benzyl hydrogens), 4.60 ppm (doublet, C-6 hydrogen), 1.50 ppm (singlet, C-2 methyl hydrogens) and 0.90 ppm (singlet, C-2 hydrogens).

C. 6-Amino-2,2-dimethyl-3-(5-tetrazolyl)penam

A stirred solution of 32.0 g. of 6-amino-2,2-dimethyl-3-(1-[p-methoxybenzyl]tetrazol-5-yl)penam p-toluenesulfonate, and 24 ml. of anisole, in 96 ml. of trifluoroacetic acid is maintained at 40 ± 1° C. for 35 min. The trifluoroacetic acid is then removed rapidly by vacuum distillation. A 120-ml. portion of ether is added to the residue, which produces a white flocculent suspension. The suspension and solvent is cooled to about 0° C., and to it is then added, portionwise, 80 ml. of 2N sodium hydroxide, giving two clear phases. The pH of the aqueous phase at this point is about 2.7. The layers are separated, and the ether phase is discarded. The pH of the aqueous phase is raised to 4.1 with 2N sodium hydroxide. This aqueous phase is then washed with 100 ml. of ether and filtered. It is combined with the corresponding aqueous phases from four other identical experiments, and the total aqueous solution is lyophilized to give crude 6-amino-2,2-dimethyl-3-(5-tetrazolyl)penam. This crude product is slurried in a small amount of water and filtered off. It is then re-suspended in water and brought into solution by raising the pH to 7.4 by the addition of sodium hydroxide solution. The clear solution is extracted with ether and the extracts are discarded. The pH of the aqueous phase is adjusted to 4.1 using dilute hydrochloric acid, and the product which precipitates is filtered off. The infrared spectrum of the product shows and absorption at 1795 $cm^{-1}$. Its NMR spectrm (in DMSO-$d_6$) shows absorptions at 5.65 ppm (doublet C-5 hydrogen), 5.20 ppm (singlet, C-3 hydrogen), 4.70 ppm (doublet, C-6 hydrogen), 1.65 ppm (singlet, C-2 methyl hydrogens) and 1.10 ppm (singlet, C-2 methyl hydrogens).

In a similar manner, the products of Examples 2, 4, 5 and 6 are converted, by the procedures of Example 7, to the intermediate, 6-amino-2,2-dimethyl-3-(tetrazolyl)penam.

EXAMPLE 8

Acylation of 6-Amino-2,2-dimethyl-3-(tetrazolyl)penam

6-(2-Phenylacetamido)-2,2-dimethyl-3-(5-tetrazolyl)penam

A flask containing 965 mg. of 6-amino-2,2-dimethyl-3-(1-[p-methoxybenzyyl]tetrazol-5-yl)penam p-toluenesulfonate, 40 drops of anisole, and 5 ml. of trifluoroacetic acid is immersed in a water-bath maintained at 35°–40° C. The progress of the reaction is followed by removing samples at intervals, and recording their nuclear magnetic resonance spectra. After about 25 min., the removal of the p-methoxybenzyl group is found to be approximately 90% complete. At this point the reaction solution is added to a rapidly-stirred, ice-cold solution of 10 ml. of pyridine in 50 ml. of chloroform. The stirring is continued for 5 min., and then 0.24 ml. of phenylacetyl chloride is added. The cooling bath is removed and the reaction mixture is stirred for a further 20 min. A 100-ml. portion of water is added, and the pH of the aqueous phase is then adjusted to 2.5 by the dropwise addition of 0.5N hydrochloric acid. The chloroform layer is separated off, washed with saturated brine, dried using anhydrous sodium sulfate and then evaporated to dryness in vacuo. The crude product thus obtained is re-dissolved in chloroform, and the solution is divided into two equal portions. To one of these portions is added an equal volume of water. The layers are stirred vigorously and the pH of the aqueous phase is raised to 6.9 by the dropwise addition of 0.1N sodium hydroxide solution. The chloroform is separated off and discarded, and then an equal quantity of fresh chloroform is added to the aqueous phase. The layers are stirred vigorously and the pH is adjusted to 2.5 using dilute hydrochloric acid. The chloroform is separated off, washed with saturated brine, dried using anhydrous magnesium sulfate and then evaporated to dryness in vacuo. This affords 197 mg. of an oily residue. The residue is re-dissolved in 3 ml. of chloroform which is then added dropwise to 30 ml. of hexane. The fluffy white solid which precipitates is filtered off, giving 80 mg. of 6-(2-phenylacetamido)-2,2-dimethyl-3-(5-tetrazolyl)penam. The infrared spectrum (KBr disc) of the product shows absorption bands at 1795 $cm^{-1}$ (β-lactam carbonyl), 1660 $cm^{-1}$ (amide I band) and 1510 $cm^{-1}$ (amide II band). The NMR spectrum (in $CDCl_3$) shows absorption bands at 7.20 ppm (broad singlet, aromaic hydrogens, 5.55 ppm (multiplet, C-5 and C-6 hydrogens), 5.15 ppm (singlet, C-3 hydrogens), 3.60 ppm (broad singlet, benzyl hydrogens), 1.40 ppm (singlet, C-2 methyl hydrogens) and 1.05 ppm (singlet, C-2 methyl hydrogens).

EXAMPLE 9

In vitro antibacterial activities for a number of compounds prepared by the procedure of Example 8 are presented below.

In Table II, the minimum inhibitory concentrations (MIC's) of compounds wherein R is hydrogen, against a strain of Streptococcus pyogenes are reported.

TABLE II

| Z | MIC (μg/ml) vs. Strep. pyogenes |
|---|---|
| 2-phenylacetyl | <0.1 |
| 3-(o-chlorophenyl)-5-methyl-4-isoxazolecarbonyl | <0.1 |
| 2-azido-2-phenylacetyl | <0.1 |
| 2-cyanoacetyl | 0.1 |
| 2-(1-tetrazolyl)acetyl | <0.39 |
| 2-phenoxyacetyl | <0.1 |
| phenoxycarbonyl | <0.1 |
| benzyloxycarbonyl | <0.1 |
| ethoxycarbonyl | <0.1 |
| acetyl | <0.1 |
| 2-bromoacetyl | <0.1 |
| 2-(4-pyridylthio)acetyl | <0.1 |
| 2-(N,N'-diethylamidinothio)acetyl | <0.1 |
| hydrogen | <0.1 |
| 3-(carbamoyl)acryloyl | <0.1 |
| 2,6-dimethoxybenzoyl | <0.2 |
| D-2-amino-2-phenylacetyl | <0.1 |
| D-2-amino-2-(m-hydroxyphenyl)acetyl | <0.1 |
| DL-2-amino-2-(3,4-dihydroxyphenyl)acetyl | <0.1 |
| L-2-amino-2-(p-hydroxyphenyl)acetyl | <0.1 |
| D-2-amino-2-(2-thienyl)acetyl | 0.1 |
| DL-2-amino-2-(p-[N,N-dimethylamino]-phenyl)acetyl | 0.39 |
| D-2-amino-2-(3-chloro-4-hydroxyphenyl)-acetyl | 0.1 |
| DL-2-amino-2-(p-chlorophenyl)acetyl | <0.1 |
| DL-2-amino-2-(m-chlorophenyl)acetyl | 0.78 |
| DL-2-amino-2-(2-bromo-5-hydroxyphenyl)-acetyl | <0.1 |
| D-2-amino-2-(m-fluorophenyl)acetyl | <0.1 |
| D-2-amino-3-methylbutyryl | 0.2 |
| D-2-amino-3-phenylpropionyl | 0.39 |
| D-2-amino-2-(p-hydroxyphenyl)acetyl | <0.1 |
| 1-aminocyclohexylcarbonyl | 25 |

What is claimed is:

1. A process for the preparation of a compound of the formula

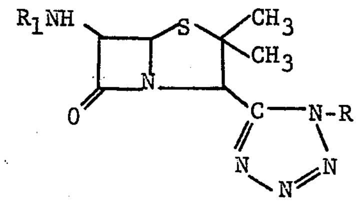

wherein R is selected from the group consisting of substituted benzyl of the formula

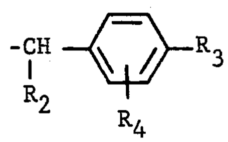

wherein $R_2$ is selected from the group consisting of hydrogen, alkyl having from one to three carbon atoms and phenyl and $R_3$ is selected from the group consisting of hydroxy, methoxy, alkanoyloxy having two to four carbon atoms, and benzyloxy and $R_4$ is selected from the group consisting of hydrogen, hydroxy, fluoro, chloro, bromo, iodo, methyl, methoxy, alkanoyloxy having from two to four carbon atoms, phenyl and benzyloxy and

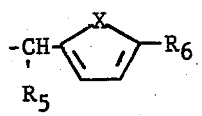

wherein $R_5$ and $R_6$ are each selected from the group consisting of hydrogen and methyl and X is selected from the group consisting of oxygen and sulfur; and $R_1$ is

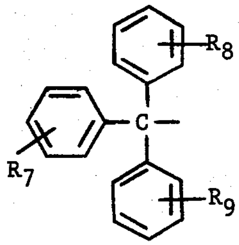

wherein $R_7$, $R_8$ and $R_9$ are each selected from the group consisting of hydrogen, chloro, bromo, fluoro, methyl, methoxy and phenyl, which comprises contacting an imino sulfonate of the formula

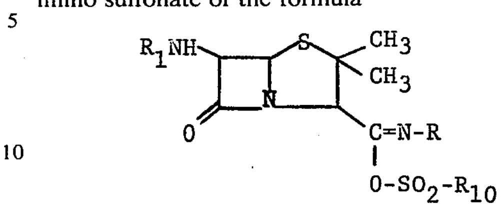

wherein $R_{10}$ is selected from the group consisting of alkyl having 1 to 4 carbon atoms, phenyl and substituted phenyl wherein said substituent is selected from the group consisting of methyl and nitro, with one to three equivalents of an azide of the formula $$MN_3$$

wherein M is selected from the group consisting of $NH_4$, Li, H and Na, at a reaction temperature of 20°–60°C. in the presence of more than one equivalent of pyridine, said imino sulfonate being dissolved in a reaction-inert solvent.

2. The process of claim 1 wherein R is p-methoxybenzyl, $R_1$ is triphenylmethyl, $R_{10}$ is selected from the group consisting of methylphenyl and alkyl having 1 to 4 carbon atoms and M is Na, at a reaction temperature of about 25° C.

3. The process of claim 2 wherein $R_{10}$ is p-methylphenyl and the reaction-inert solvent is chloroform.

4. The process of claim 2 wherein $R_{10}$ is methyl and the reactioninert solvent is chloroform.

5. The process of claim 1 wherein R is 2-furfuryl, $R_1$ is triphenylmethyl, $R_{10}$ is selected from the group consisting of methylphenyl and alkyl having 1 to 4 carbon atoms, and M is Na at a reaction temperature of about 25° C.

6. The process of claim 5 wherein $R_{10}$ is p-methylphenyl and the reaction-inert solvent is chloroform.

7. The process of claim 5 wherein $R_{10}$ is methyl and the reactioninert solvent is chloroform.

* * * * *

UNITED STATES PATENT AND TRADEMARK OFFICE
CERTIFICATE OF CORRECTION

PATENT NO. : 3,957,811

DATED : May 18, 1976

INVENTOR(S) : Susumu Nakanishi

It is certified that error appears in the above-identified patent and that said Letters Patent are hereby corrected as shown below:

Col. 6, line 56, "the" should read -- The --.

Col. 7, line 33, "cmpound" should read -- compound --.

Col. 12, line 20, (before the table) should read

-- 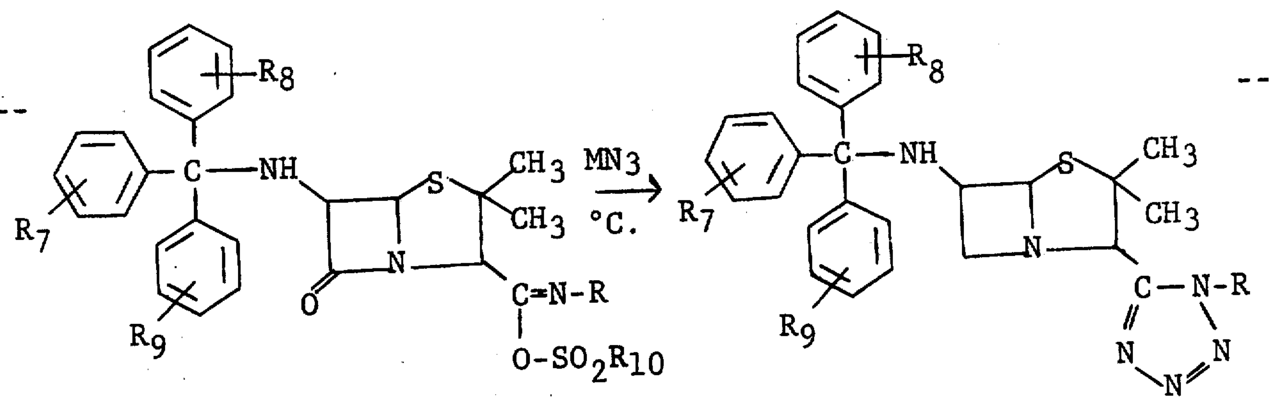 --

UNITED STATES PATENT AND TRADEMARK OFFICE
CERTIFICATE OF CORRECTION

PATENT NO. : 3,957,811
DATED : May 18, 1976
INVENTOR(S) : Susumu Nakanishi

It is certified that error appears in the above-identified patent and that said Letters Patent are hereby corrected as shown below:

Col. 13, line 15, (before the table) should read

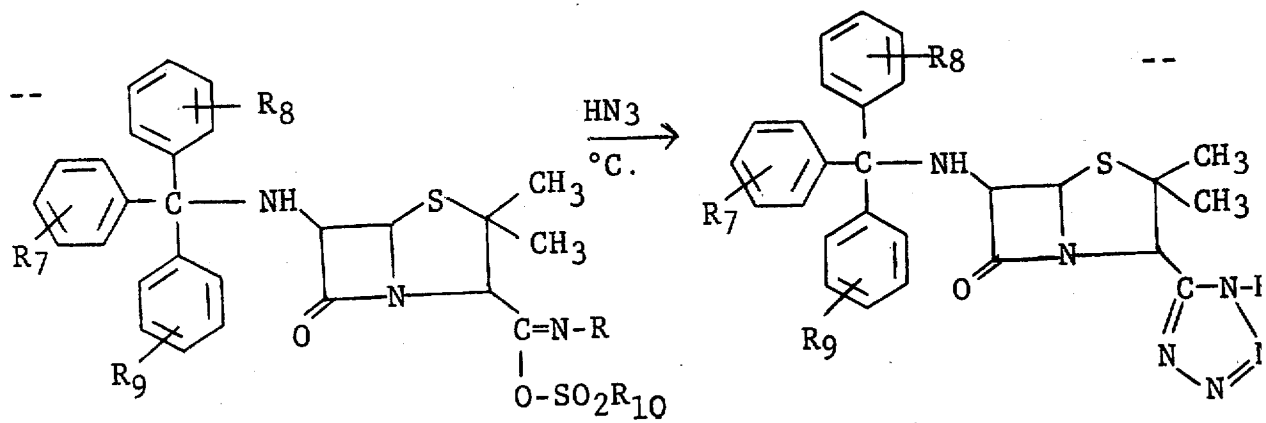

Col. 15, line 22, "and" should read -- an --.

Col. 16, line 13, "aromaic" should read -- aromatic --.

Col. 18, line 34, "reactioninert" should read -- reaction-inert --;

line 43, "reactioninert" should read -- reaction-inert --.

Signed and Sealed this

Ninth Day of November 1976

[SEAL]

Attest:

RUTH C. MASON
*Attesting Officer*

C. MARSHALL DANN
*Commissioner of Patents and Trademarks*